(12) United States Patent
Zafar et al.

(10) Patent No.: US 11,860,146 B2
(45) Date of Patent: Jan. 2, 2024

(54) SOIL NUTRIENT SENSING PLATFORM (71) Applicant: INTERNATIONAL BUSINESS MACHINES CORPORATION, Armonk, NY (US)

(72) Inventors: Sufi Zafar, Briarcliff Manor, NY (US); Hendrik F. Hamann, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 330 days.

(21) Appl. No.: 16/883,976

(22) Filed: May 26, 2020

(65) Prior Publication Data
US 2021/0372983 A1 Dec. 2, 2021

(51) Int. Cl.
| G01N 33/24 | (2006.01) |
| G01K 7/02 | (2021.01) |
| A01G 25/16 | (2006.01) |
| G01S 19/03 | (2010.01) |

(52) U.S. Cl.
CPC ........... G01N 33/246 (2013.01); A01G 25/16 (2013.01); G01K 7/023 (2013.01); G01S 19/03 (2013.01); G01N 2033/245 (2013.01)

(58) Field of Classification Search
CPC ........... G01N 33/246; G01N 2033/245; A01G 25/16; A01G 25/167; G01K 7/023; G01S 19/03
See application file for complete search history.

(56) References Cited

U.S. PATENT DOCUMENTS

| 6,401,742 | B1* | 6/2002 | Cramer ............... A01G 25/167 239/63 |
| 9,733,206 | B2 | 8/2017 | Miller et al. |
| 2015/0323491 | A1* | 11/2015 | Miller ............... G01N 27/4035 205/789 |
| 2019/0101505 | A1 | 4/2019 | Liu et al. |
| 2019/0285608 | A1 | 9/2019 | Laird et al. |
| 2020/0096474 | A1* | 3/2020 | Mansergh ............ G01N 33/246 |
| 2020/0132655 | A1 | 4/2020 | Kusiek et al. |
| 2020/0150073 | A1* | 5/2020 | Zafar .................. G01N 33/025 |
| 2020/0257318 | A1* | 8/2020 | Nahuel-Andrejuk ... B64C 25/32 |
| 2020/0378885 | A1* | 12/2020 | Yang .................... G01N 17/04 |
| 2021/0356425 | A1* | 11/2021 | Zhang ..................... G01N 1/14 |

FOREIGN PATENT DOCUMENTS

CN 201069429 Y * 6/2008

OTHER PUBLICATIONS

Zafar, S. et al., "Comparison Between Field Effect Transistors and Bipolar Junction Transistors as Transducers in Electrochemical Sensors"; Scientific Reports (2017); vol. 7:41430; 10 pgs.

* cited by examiner

*Primary Examiner* — Chad G Erdman
(74) *Attorney, Agent, or Firm* — Intelletek Law Group, PLLC; Gabriel Daniel, Esq.

(57) ABSTRACT

A device includes a housing with a reference electrode having a metal plug extending through the housing. One or more sensing surfaces are disposed on an exterior of the housing, where the one or more sensing surfaces are configured to perform a nutrient measurement of a soil. A moisture sensor is disposed on an exterior of the housing for detecting a moisture level of the soil.

20 Claims, 10 Drawing Sheets

SOIL NUTRIENT SENSING PLATFORM

BACKGROUND

Technical Field

The present disclosure generally relates to agriculture apparatus, and more particularly, to methods and systems for making subterranean soil nutrient measurements.

Description of the Related Art

Soil pH generally refers to the degree of soil acidity or alkalinity. In mathematical terms, pH is a −log 10 measurement of the concentration of hydrogen ions (H+) present in a solution of soil. The pH scale is measured from 0 to 14, with a pH of approximately 7 being considered neutral. A pH measurement of less than 7 is considered acidic while a pH of greater than 7 is considered alkaline. Commonly, the closer a soil solution is to 0, the more acidic the soil solution is due to the higher the concentration of hydrogen ions present in the soil. Conversely, pH measurements greater than 7 indicate that a soil solution is more alkaline due a lower concentration of hydrogen ions present in the soil solution.

The pH differences in soils may be quite variable. Certain soil compositions may comprise a higher natural buffering capacity and therefore be more resistant to decreases in pH. Soil pH is important because pH affects the soil's physical, chemical and biological properties as well as plant growth. The nutrition, growth and yields of most crops are observable as a function of pH. Crop yields generally decrease in soils with a low pH and rise as the pH of soils increase, up to an optimal level, typically around a neutral to slightly alkaline pH.

Soil pH and soil nutrient measurements are used to ensure an optimal pH and that neither too little nor too much nutrients are present. The proper levels of nitrogen, potassium and potassium, as well as soil pH, are required for optimum agriculture performance.

SUMMARY

According to various embodiments, a device comprises a housing with a reference electrode having a metal plug extending through the housing. One or more sensing surfaces are disposed on an exterior of the housing, where the one or more sensing surfaces are configured to perform a nutrient measurement of a soil. A moisture sensor is also disposed on an exterior of the housing. The device can be implanted in the ground for measuring nutrients in real time to ensure proper fertilizer application. The moisture sensor can ensure the soil has adequate moisture to obtain an accurate measurement.

In one embodiment, automation circuitry is disposed in the housing and configured to receive signals from the one or more sensing surfaces, the reference electrode, and the moisture sensor.

In one embodiment, the device includes at least one of soil pH or soil concentration of one or more ions (e.g. nitrate ions, phosphate ions, chloride, Ca++). The device, when configured with multiple sensing surfaces, can make multiple, different soil property measurements.

In one embodiment, the one or more sensing surfaces measure temperature. By sensing temperature, the measurements can be corrected for temperature to provide more accurate data.

In one embodiment, the device further includes a water reservoir configured to expel water through one or more water outlets disposed adjacent the one or more sensing surfaces when the moisture sensor detects a moisture level below a predetermined minimum. The water reservoir can be used to provide adequate moisture levels to ensure measurements.

In one embodiment, the moisture sensor, the metal plug, and the one or more sensing surfaces are disposed at a bottom surface of the housing.

In one embodiment, the moisture sensor, the metal plug, and the one or more sensing surfaces are disposed along a side of the housing adjacent a bottom surface of the housing at a first height along the side of the housing.

In one embodiment, a second moisture sensor, a second metal plug of a second reference electrode, and a second set of one or more sensing surfaces are disposed along a side of the housing at a second height above the first height along the side of the housing. The use of two different locations along the side of the housing permits data to be obtained at different soil depths.

In one embodiment, the device further includes a water reservoir operable to expel water via a first set of one or more water outlets disposed adjacent the one or more sensing surfaces and via a second set of one or more water outlets disposed adjacent the second set of one or more sensing surfaces when the moisture sensor and the second moisture sensor detects a moisture level below a predetermined minimum.

In one embodiment, the automation circuitry includes a wireless transceiver configured to send and receive data from the soil nutrient measurement device. This allows the user to get data, in real time, as the device is implemented.

In one embodiment, the automation circuitry includes a processor and memory for storing data received from the reference electrode and the one or more sensing surfaces.

In one embodiment, the automation circuitry includes a GPS device for detecting a location of a measurement made by the one or more sensing surfaces. This provides the ability of the user to know where each measurement was obtained.

In one embodiment, the soil nutrient measurement device further includes a drone device operable to move the soil nutrient measurement device to a desired location to perform a measurement.

According to various embodiments, a method of performing a soil nutrient measurement comprises providing a reference electrode having a metal plug extending through a surface of a housing, performing a plurality of soil nutrient measurements by a plurality of sensing surfaces on an exterior of the housing, and sensing a moisture level from a moisture sensor on the exterior of the housing. The device can be implanted in the ground for measuring nutrients in real time to ensure proper fertilizer application.

According to various embodiments, a soil nutrient measurement device comprises a housing with a first and second measurement system. The first measurement system includes a first reference electrode having a metal plug extending through a side surface at a first location adjacent a bottom surface of the housing. A first plurality sensing surfaces are on an exterior of the side surface of the housing adjacent the bottom surface thereof. The first plurality of sensing surfaces are configured to perform a first plurality of soil nutrient measurements. A first moisture sensor on the exterior of the side surface of the housing is adjacent the bottom surface thereof. The first measurement system including a second reference electrode having a metal plug extends through the side surface at a second location above the first location. A second plurality of sensing surfaces are on an exterior of the side surface of the housing at the second location, the second plurality of sensing surfaces configured to perform a second plurality of soil nutrient measurements. A second moisture sensor is on the exterior of the side surface of the housing at the second location. Automation circuitry is configured to receive signals from the first and second plurality of sensing surfaces, the first and second reference electrodes and the first and second moisture sensors. The device can be implanted in the ground for measuring nutrients in real time to ensure proper fertilizer application. The use of the first and second measurement systems permits measurements to occur at multiple soil depths.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

DETAILED DESCRIPTION

In the following detailed description, numerous specific details are set forth by way of examples to provide a thorough understanding of the relevant teachings. However, it should be apparent that the present teachings may be practiced without such details. In other instances, well-known methods, procedures, components, and/or circuitry have been described at a relatively high-level, without detail, to avoid unnecessarily obscuring aspects of the present teachings.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

As used herein, a soil "nutrient" measurement refers to a measurement of ions in the soil, soil pH and soil moisture. Ion measurement can include nitrogen, nitrate, potassium, phosphate, chloride, and the like.

The present disclosure generally relates to a soil nutrient measurement platform that includes a soil nutrient measurement device having a housing with a plurality of elements extending to an exterior of the housing. These elements include a metal plug of a reference electrode, one or more sensing electrodes, a moisture sensor and one or more optional water outlets. Automation circuitry may be included inside the housing to receive signals from the reference electrode, the one or more sensors, and the moisture sensors, and determine levels of certain nutrients and/or soil pH, as described in greater detail below.

Figure 1:
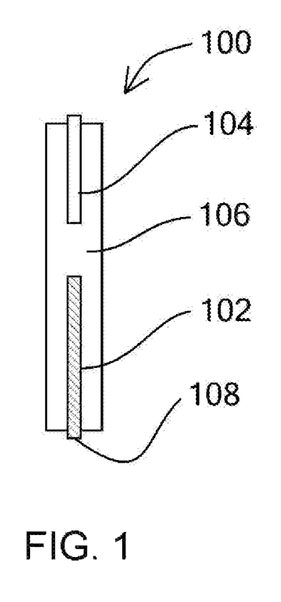
FIG. 1 is a cross-sectional view of a reference electrode usable in the soil nutrient sensing platform, according to an illustrative embodiment.

Referring to FIG. 1, a reference electrode 100 is shown. The reference electrode 100 can include a metal plug 102 that extends beyond a sealed bottom 108 thereof. A reference metal, such as a titanium nitride (TiN) plate 104 may extend from inside the reference electrode 100 to extend out a top end thereof. A buffer solution 106 may be present inside the reference electrode 100, providing liquid communication between the metal plug 102 and the titanium nitride plate 104.

Figure 2:
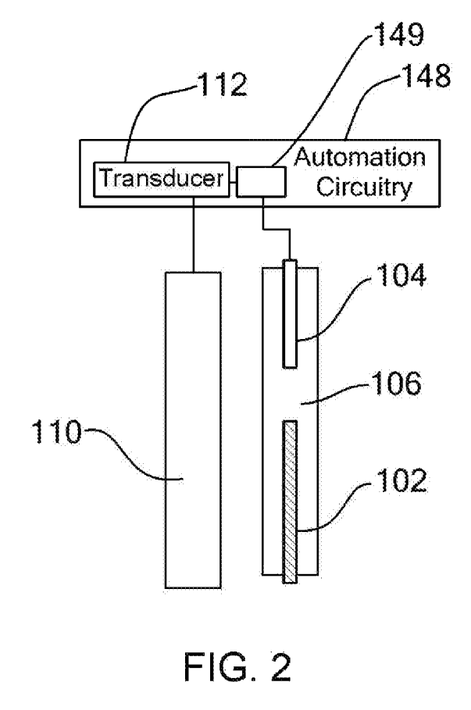
FIG. 2 a schematic representation of a chemical sensor connected to the reference electrode of FIG. 1, according to an illustrative embodiment.

Referring also to FIG. 2, the reference electrode 100 may be electrically connected to a voltage source, such as power supply 149 as part of automation circuitry 148. A sensing surface 110 can be connected to a transducer 112. The transducer may be a bipolar junction transistor (BJT), a field effect transistor (FET), or the like. The change in the surface potential of the sensing surface 110 due to binding of target ions causes the signal at the transducer 112 to change. The reference electrode 100 applies a voltage to the medium in which it is inserted, such as the soil. This can be used to determine a desired measurement, such a pH, nutrient content, or the like. While the Figures illustrate a single transducer block 112, it should be understood that where there are multiple sensing surfaces 110, each sensing surface 110 may be connected to its own transducer 112.

Figure 3:
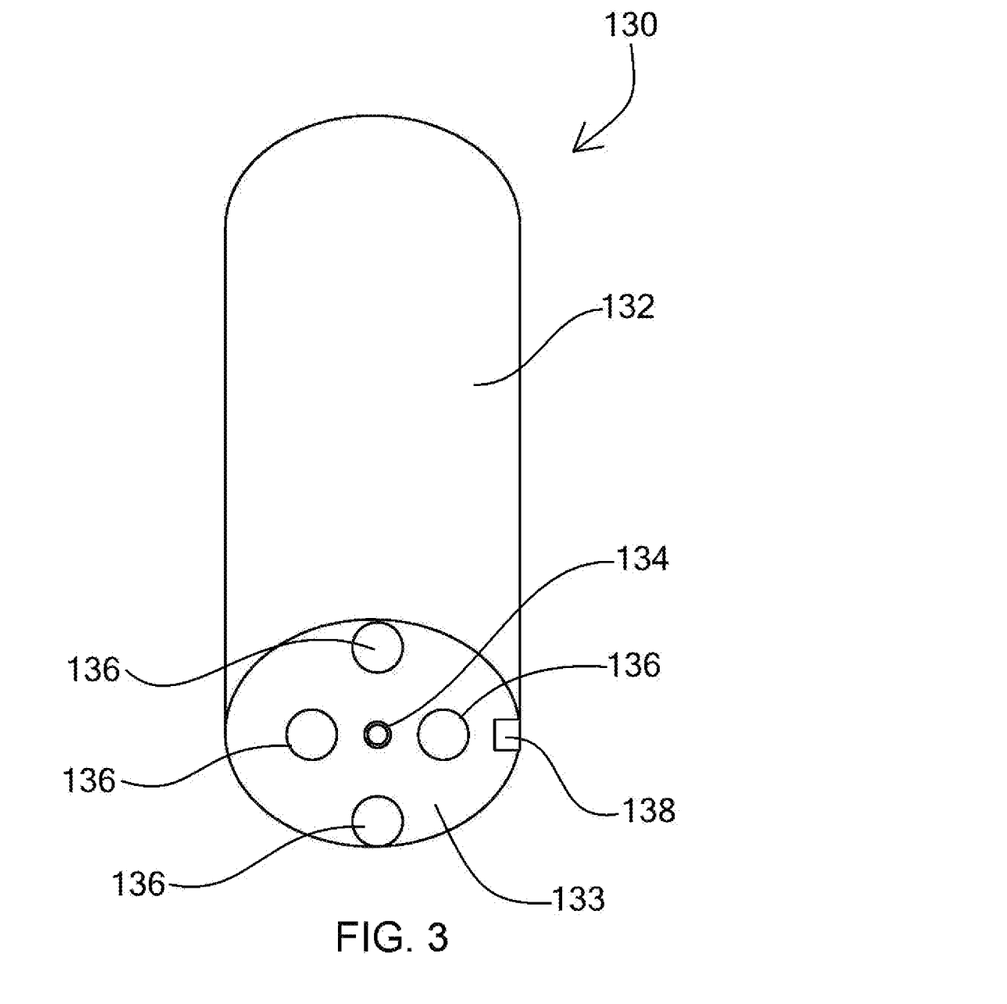
FIG. 3 is a bottom perspective view of a soil nutrient sensing device, according to an illustrative embodiment.
Figure 4:
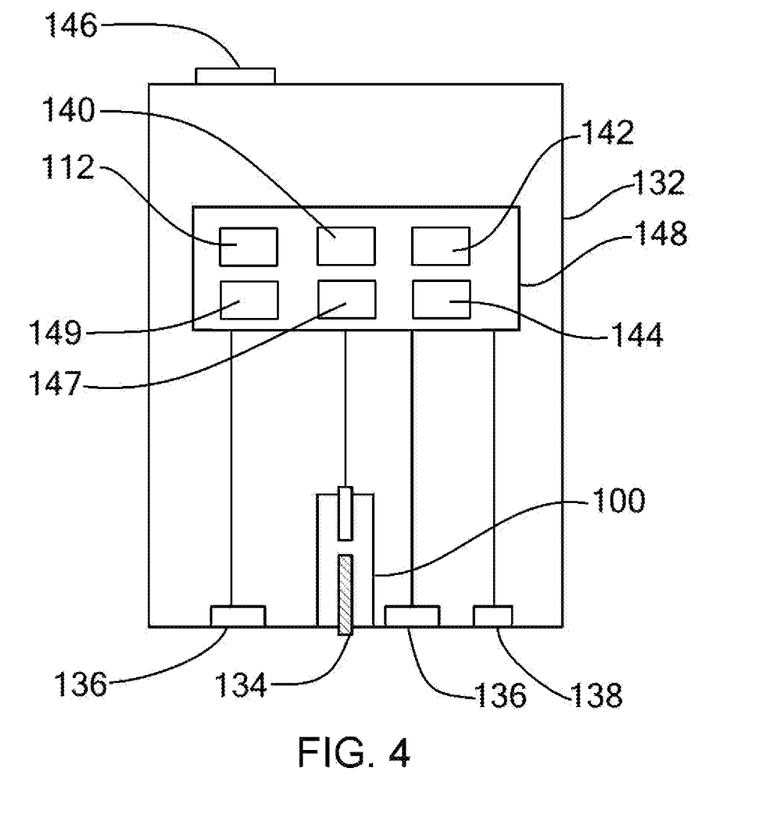
FIG. 4 is a cross-sectional schematic representation of the soil nutrient sensing device of FIG. 3, according to an illustrative embodiment.

Referring now to FIGS. 3 and 4, a soil nutrient measurement device 130 can include a housing 132 having a plug surface 134 penetrating from the housing 132 at a bottom surface 133 thereof. The plug surface 134 is the bottom portion of the metal plug 102 of the reference electrode 100 as shown in FIGS. 1 and 2. Further, one or more sensing surfaces 136 can penetrate through the bottom surface 133 of the housing 132. The one or more sensing surfaces 136 may be similar or differently shaped surfaces, including planar surfaces, rod-shaped protrusions, or the like. Finally, a moisture sensor 138 can penetrate through the bottom surface 133 of the housing 132. The one or more sensing surfaces 136 may include four sensing surfaces 136, as shown in FIG. 3. Each sensing surface 136 may be configured to make a different measurement. For example, the sensing surfaces 136 of FIG. 3 may be configured to measure one or more of pH, nitrogen levels, phosphorus levels, potassium levels, chloride levels, temperature, and the like, for example. The sensing electrodes can be formed from an appropriate material that specifically binds the target ion to make the various measurements. For example, the sensing electrodes for pH may be constructed out of or coated with titanium nitride.

The housing 132 may be a tubular material, such as a PVC pipe, metal tube, or the like. The side of the housing 132 may vary, depending on the particular application, and may be from about 1-inch to over 6-inches. The housing 132 may be hollow or may be filled with a shock absorbing material or fluid. While the Figures show a round housing, it should be understood that the housing may be configured in various shapes, sizes, and configurations based on the type of soil/terrain.

Referring to FIG. 4, an automation circuitry 148 may interconnect the one or more sensing surfaces 136, the moisture sensor 138 and the reference electrode 100. The automation circuitry 148 can receive signals from these components and determine the appropriate measurements, such as pH, nutrient levels, moisture levels, temperature, or the like. While FIG. 4 shows the one or more sensing surfaces 136 simply connected to the automation circuitry 148, it should be understood that each of the one or more sensing surfaces 136 are connected to a transducer 112 within the automation circuitry 148. Further, while FIG. 4 shows the reference electrode 100 simply connected to the automation circuitry 148, it should be understood that the reference electrode is connected to the power supply 149, as illustrated in FIG. 2.

The automation circuitry 148 can further include a wireless transceiver 140 for sending and receiving data, a processor 142 for executing program code stored in a memory 144, such program code configured at least for determining the appropriate measurements from the signals received from the various sensors. The memory 144 may further be used to store the data from the sensors or the processed data of the appropriate measurements determined from the signals from the sensors. The automation circuitry 148 can also include a GPS locating device 147, permitting measurements to be linked with a specific location the measurement was performed. Finally, the automation circuitry 148 can include the transducer 112, or the set of transducers, as discussed above.

In some embodiments, an external notification device 146 can be provided on the exterior of the housing. The notification device 146 can provide a visual or audio notification to the user of a particular nutrient level or moisture level. For example, the notification device 146 can light green to illustrate proper fertilizer application (e.g., nutrient levels within a predetermined range), red for too low fertilizer application, yellow for low moisture levels, or the like. In other embodiments, a user may have a portable electronic device to receive data, in real time, from the wireless transceiver 140. In other embodiments, the user may make measurements and analyze those at a later time.

Figure 5:
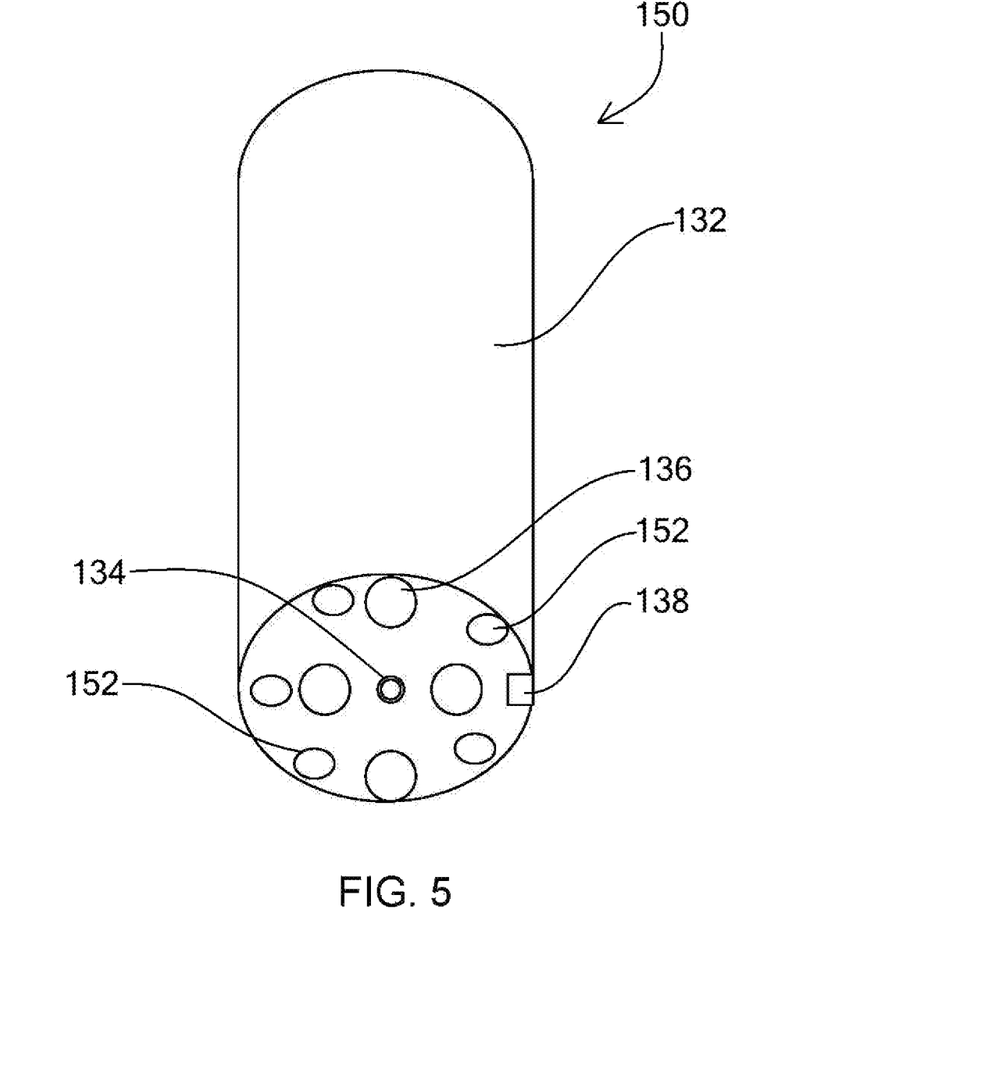
FIG. 5 is a bottom perspective view of the soil nutrient sensing device of FIG. 3 including a water reservoir and water outlets, according to an illustrative embodiment.
Figure 6:
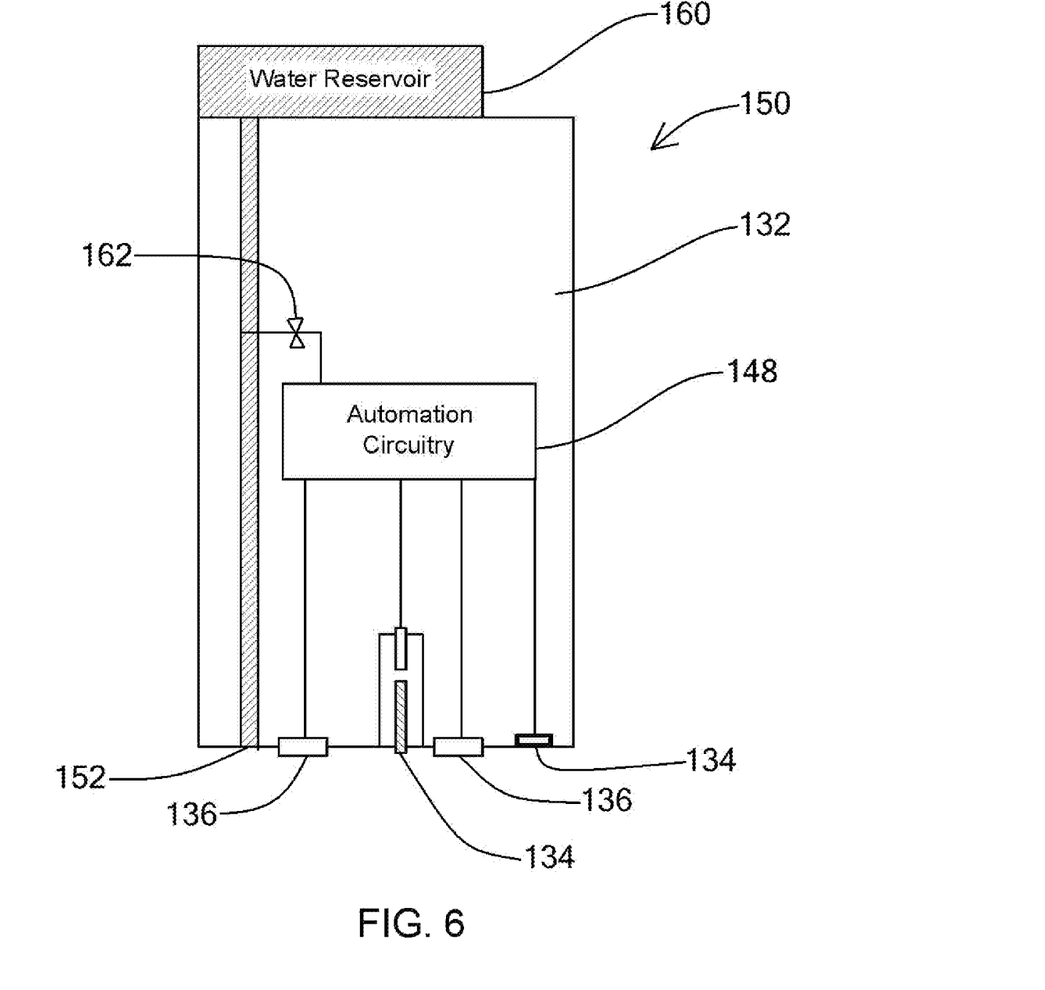
FIG. 6 is a cross-sectional schematic representation of the soil nutrient sensing device of FIG. 5.

Referring now to FIGS. 5 and 6, the soil nutrient measurement device 130 of FIGS. 3 and 4 can be configured with a water reservoir 160 that can provide water to soil when the moisture sensor 138 detects a moisture level below which the sensing surfaces 136 may make an accurate measurement. One or more water outlets 152 of the soil nutrient measurement device 150 can be provided at the bottom surface 133 of the housing 132 to expel water from the water reservoir 160 when needed to make an accurate measurement. A valve 162 may be controlled by the automation circuitry 148 to control the flow of water from the water reservoir 160 to the water outlets 152.

Figure 7:
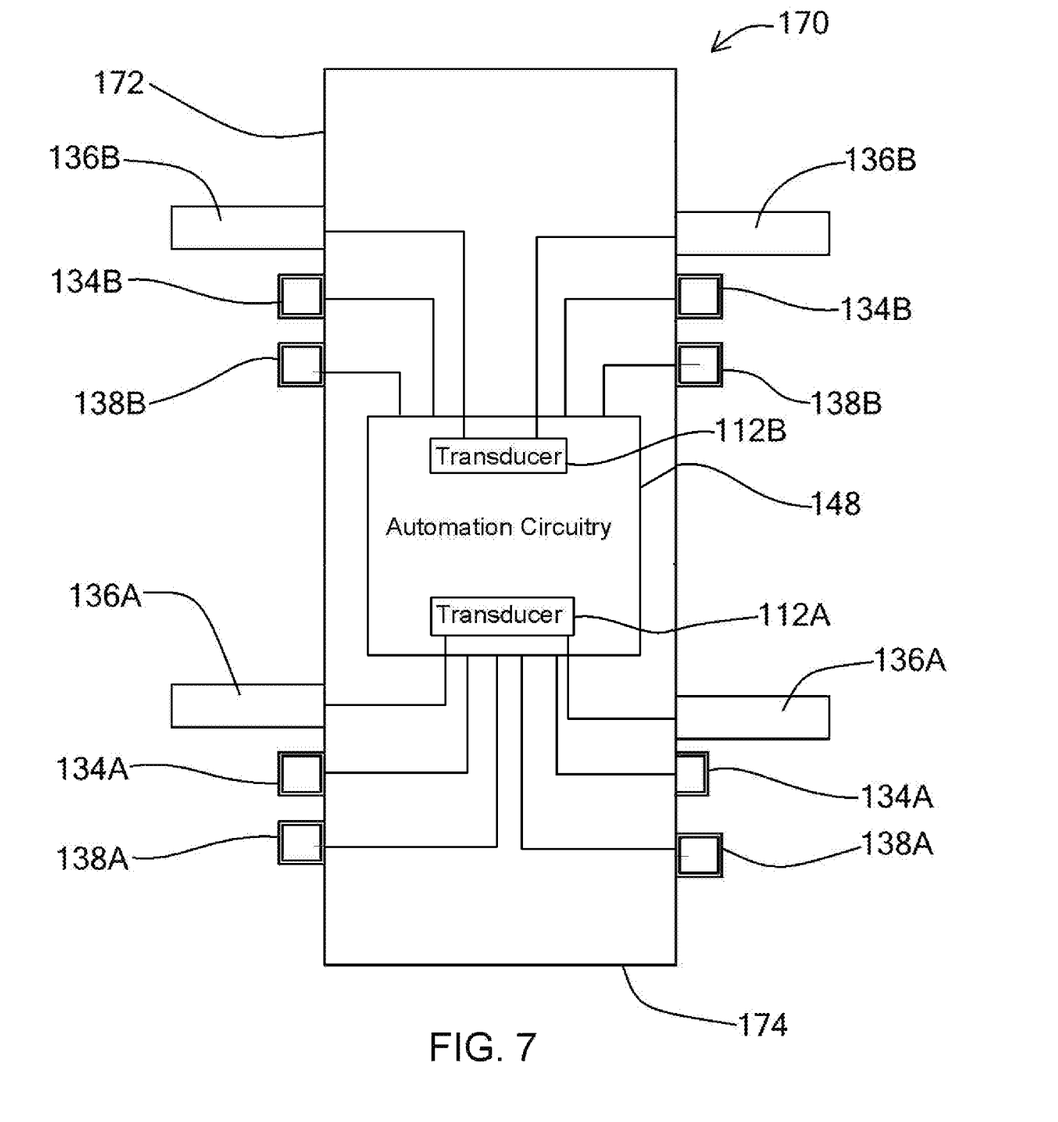
FIG. 7 is a cross-sectional schematic representation of a soil nutrient sensing device configured to perform measurements at multiple depths, according to an illustrative embodiment.

Referring now to FIG. 7, a soil nutrient measurement device 170 can be configured in a similar manner to those described above, except that the sensing surfaces 136A, 136B, the moisture sensors 138A, 138B, and the metal plug 134A, 134B, may be disposed at sides of a housing 172 of the measurement device 170. A first set of sensing surfaces 136A, moisture sensors 138A and a metal plug 134A can be disposed at a lower end of the housing 172. A second set of sensing surfaces 136B, moisture sensors 138B and a metal plug 134B can be disposed at an upper end of the housing 172. Thus, the measurement device 170 can provide measurements at more than one depth. While two depths for making measurements are shown in FIG. 7, additional sets of sensing surfaces, moisture sensors and the metal plug can be provided at various locations along a longitudinal length of the measurement device 170, or at the bottom surface of the measurement device 170, to provide data at more than two depths, thereby providing different soil parameters at different depths at a same topographical location.

A lower transducer 112A, or set of lower transducers where there are multiple lower sensing surfaces, and an upper transducer 112B, or a set of upper transducers where there are multiple upper sensing surfaces can be provided to receive signals from the lower and upper sensing surfaces and metal plugs of the reference electrodes to make the appropriate measurements, as discussed above. While not the automation circuitry 148 does not identify specific components for clarity, the automation circuitry 148 can be similar to that described above with reference to FIG. 4 described above.

Figure 8:
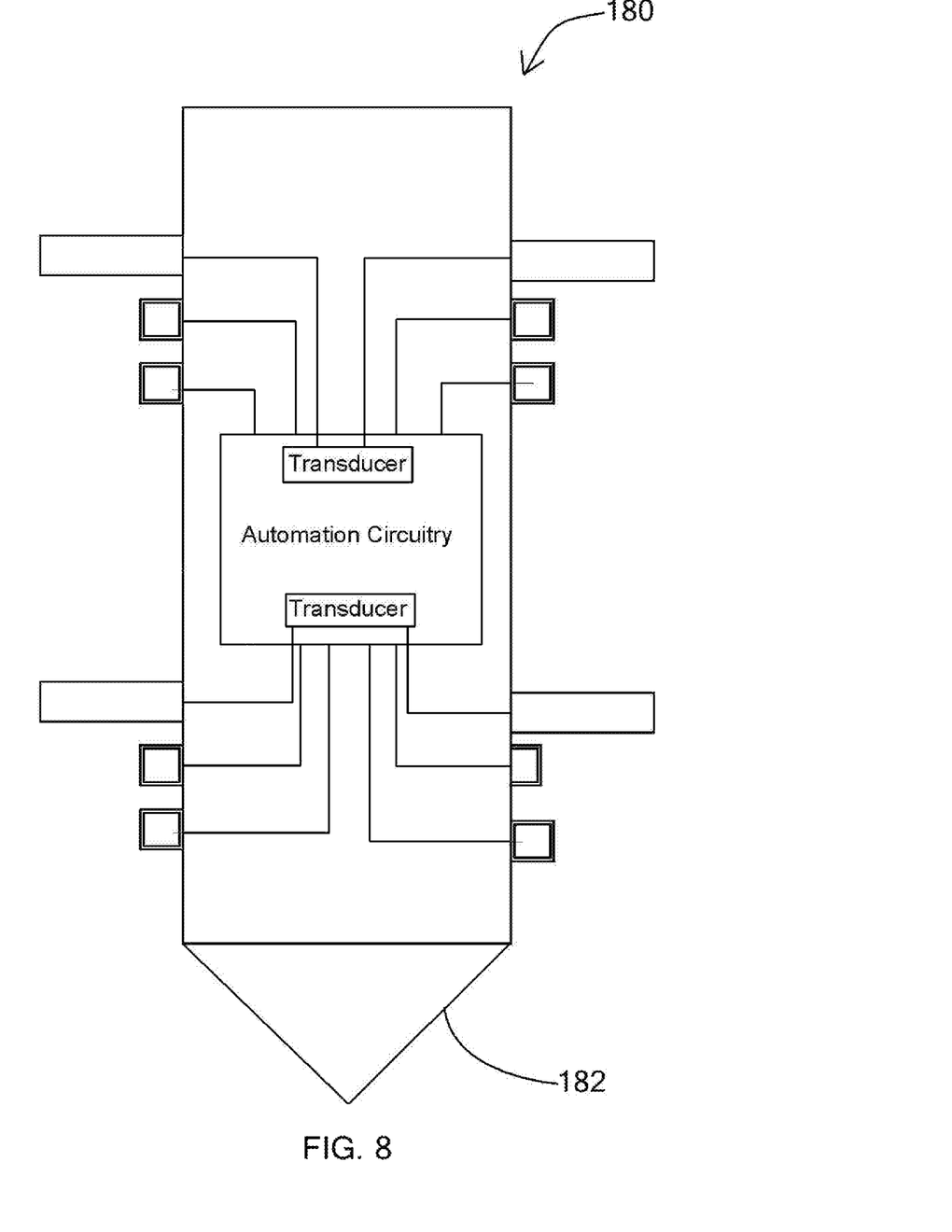
FIG. 8 is a cross-sectional schematic representation of the soil nutrient sensing device of FIG. 7 with an optional soil penetrating tip, according to an illustrative embodiment.

Referring to FIGS. 7 and 8, the bottom surface 174 of the housing 172 may lack any sensors protruding therethrough. In one embodiment, the bottom surface 174 may include a soil penetrating shaped tip 182, such as a pointed tip, as shown in FIG. 8. Such a tip 182 can help the measurement device 180 penetrate the soil to achieve the appropriate depths for making multiple measurements at multiple depths.

Figure 9:
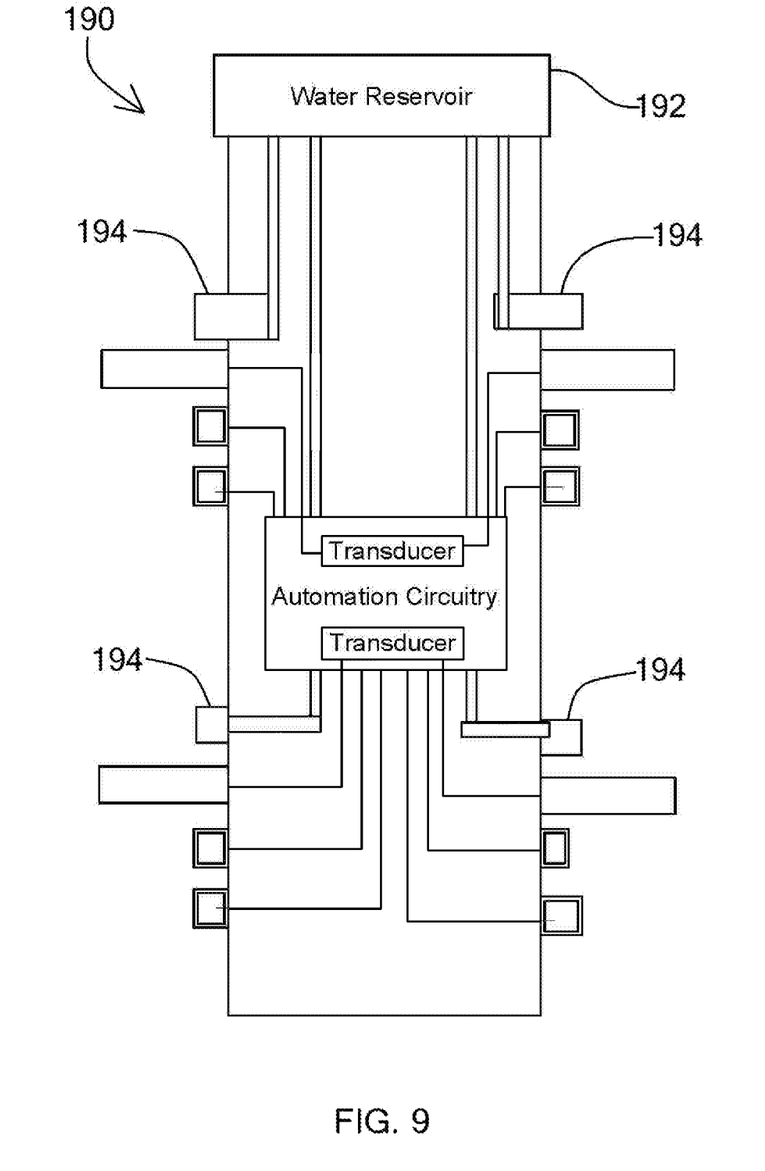
FIG. 9 is a cross-sectional schematic representation of the soil nutrient sensing device of FIG. 7, including a water reservoir and water outlets, according to an illustrative embodiment.

Referring now to FIG. 9, a soil nutrient measurement device 190 can be similar to that of the measurement device 170 of FIG. 7, with the addition of a water reservoir 192 that can feed water to a plurality of water outlets 194. The operation of the water reservoir 192 is similar to that described above with respect to FIG. 6.

Similar to that described with reference to FIGS. 2 and 4, with reference to FIGS. 6 through 9, the one or more sensing surfaces 136 are shown to simply connect to the transducers 112A, 112B within the automation circuitry 148. It should be understood that each of the one or more sensing surfaces 136 are connected to a transducer within the automation circuitry 148. Further, while the reference electrode 100 and the moisture sensors 138 are shown simply connected to the automation circuitry 148, it should be understood that the reference electrode is connected to the power supply 149, as illustrated in FIG. 2. The circuitry for operating the sensor, which includes the transducer 112 and the reference electrode, is included in the automation circuitry 148.

Figure 10:
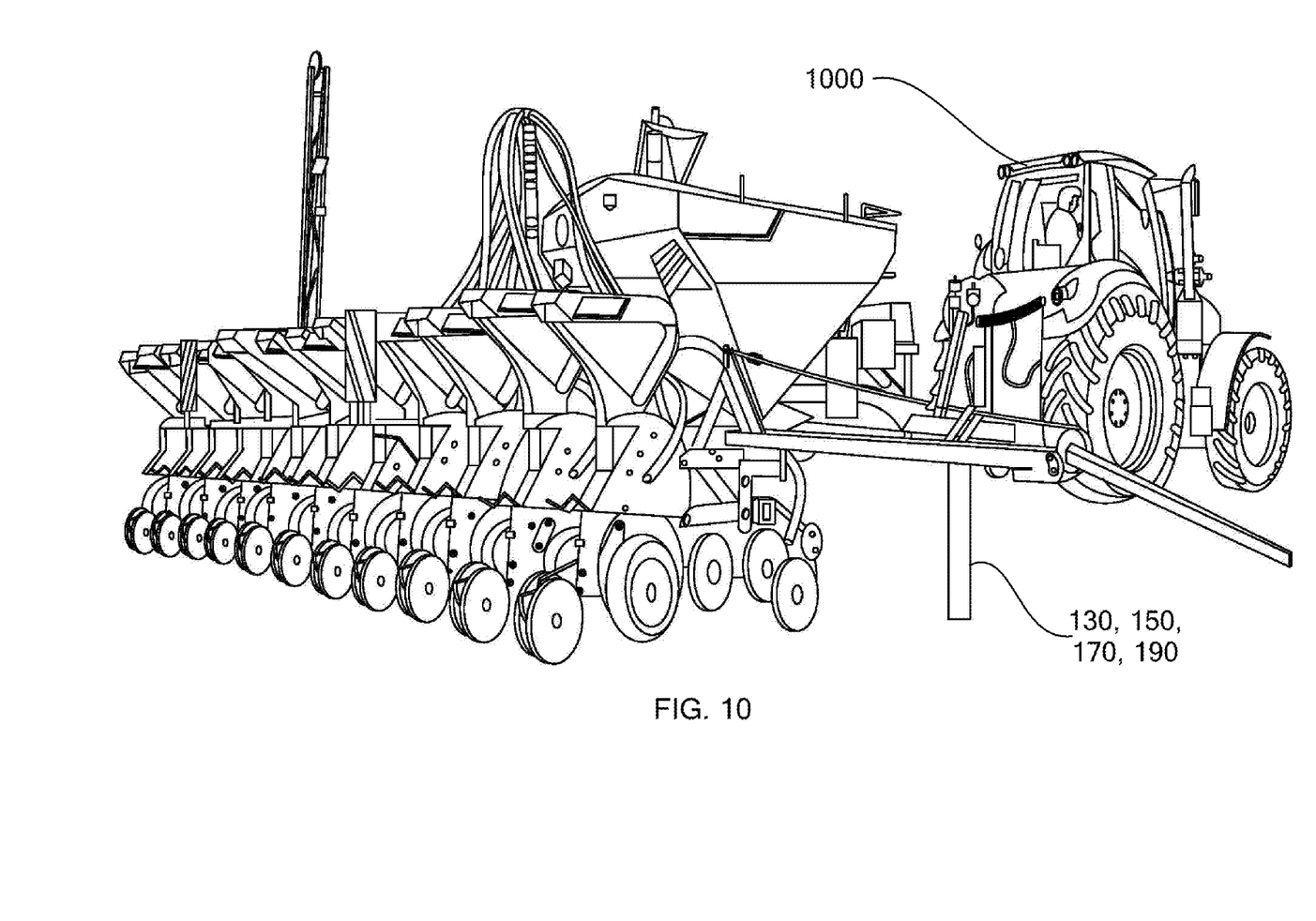
FIG. 10 is a perspective view of a tractor-implemented soil nutrient sensing device, according to an illustrative embodiment.

Referring to FIG. 10, the soil nutrient measuring device 130, 150, 170, 190 can be attached to a tractor 1000. As the tractor 1000 tills a field, the tractor 1000 can be intermittently stopped and the device 130, 150, 170, 190 can be lowered into the ploughed soil. Soil moisture can be measured and, if the moisture is too low, then water can be injected to wet the soil. After a wait of a fixed amount of time, nutrients (nitrate, pH and other ions) can be measured at that location. Based on the nutrient reading, fertilizer can be applied to the field in an appropriate amount, thus avoiding over or under fertilization.

Figure 11:
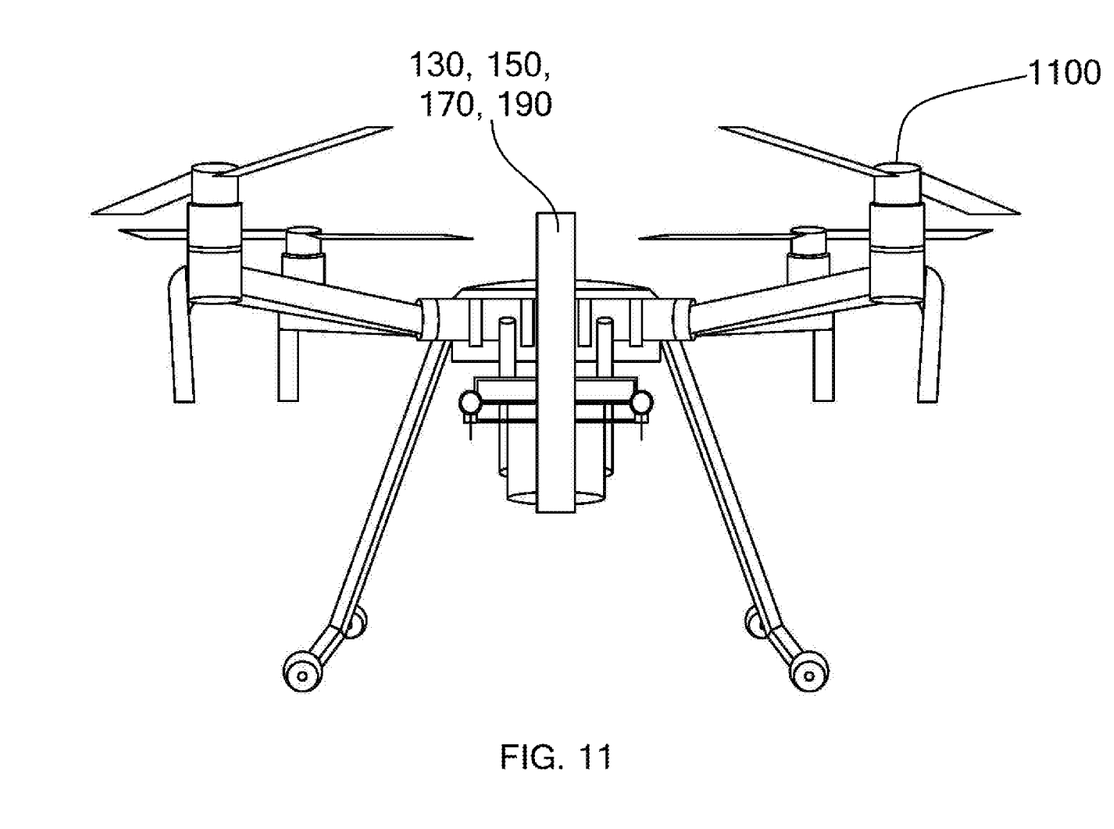
FIG. 11 is a perspective view of a drone-deployment of the soil nutrient sensing device, according to an illustrative embodiment.

Referring to FIG. 11, the soil nutrient measuring device 130, 150, 170, 190 can be attached to a drone 1100. The drone 1100 can be used to lower the device 130, 150, 170, 190 into a field to measure soil nutrients. As discussed above, GPS technology may be used to track the location of the measurements so that a user can determine specific locations that may require fertilization.

CONCLUSION

The descriptions of the various embodiments of the present teachings have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A device comprising:
    a housing;
    a reference electrode having a metal plug extending through the housing and a reference metal comprising titanium nitride (TiN) in liquid communication with the metal plug;
    one or more sensing surfaces on an exterior of the housing, the one or more sensing surfaces configured to perform a nutrient measurement of a soil; and
    a moisture sensor on an exterior of the housing.

2. The device of claim 1, wherein the soil nutrient measurement includes at least one of a pH or a concentration of one or more ions of the soil.

3. The device of claim 1, wherein the one or more sensing surfaces measure a temperature of the soil.

4. The device of claim 1, further comprising a water reservoir configured to expel water adjacent the one or more sensing surfaces when the moisture sensor detects a moisture level below a predetermined minimum.

5. The device of claim 1, wherein the moisture sensor, the metal plug, and/or the one or more sensing surfaces are disposed at a bottom surface of the housing.

6. The device of claim 1, wherein the moisture sensor, the metal plug, and the one or more sensing surfaces are disposed along a side of the housing adjacent a bottom surface of the housing at a first height along the side of the housing.

7. The device of claim 6, wherein a second moisture sensor, a second metal plug of a second reference electrode, and a second set of one or more sensing surfaces are disposed along a side of the housing at a second height above the first height along the side of the housing.

8. The device of claim 7, further comprising a water reservoir configured to expel water via a first set of one or more water outlets disposed adjacent the one or more sensing surfaces and a second set of one or more water outlets disposed adjacent the second set of one or more sensing surfaces when the moisture sensor and the second moisture sensor detect a moisture level below a predetermined minimum.

9. The device of claim 1, further comprising automation circuitry configured to receive signals from the one or more sensing surfaces, the reference electrode and the moisture sensor.

10. The device of claim 9, wherein the automation circuitry includes a wireless transceiver configured to send and receive data.

11. The device of claim 9, wherein the automation circuitry includes a processor and memory for storing data received from the reference electrode and the one or more sensing surfaces.

12. The device of claim 9, wherein the automation circuitry includes a GPS device for detecting a location of a measurement made by the one or more sensing surfaces.

13. The device of claim 1, wherein the device is a drone device configured to move to a desired location to perform a measurement.

14. A method of performing a soil nutrient measurement comprising:
providing a reference electrode having a metal plug extending through a surface of a housing and a reference metal comprising titanium nitride (TiN) in liquid communication with the metal plug;
performing a plurality of soil nutrient measurements by a plurality of sensing surfaces on an exterior of the housing; and
sensing a moisture level from a moisture sensor on the exterior of the housing.

15. The method of claim 14, further comprising, upon determining that the moisture level is below a predetermined minimum, expelling water from a water reservoir to one or more water outlets disposed adjacent the plurality of sensing surfaces.

16. The method of claim 14, further comprising:
determining a location of a measurement made by the one or more sensing surfaces by a global positioning device (GPS); and
sending data from the soil measurement, including the location from the GPS, to an external device via a wireless transceiver disposed within the housing.

17. A device comprising:
a first measurement system including:
a first reference electrode having (i) a metal plug extending through a side surface at a first location adjacent a bottom surface of a housing and (ii) and a reference metal comprising titanium nitride (TiN) in liquid communication with the metal plug;
a first plurality of sensing surfaces on an exterior of the side surface of the housing adjacent the bottom surface thereof, the first plurality of sensing surfaces configured to perform a first set of one or more soil nutrient measurements; and
a first moisture sensor on the exterior of the side surface of the housing adjacent the bottom surface thereof;
a second measurement system including:
a second reference electrode having a metal plug extending through the side surface at a second location above the first location of the housing;
a second plurality sensing surfaces on an exterior of the side surface of the housing at the second location, the second plurality of sensing surfaces configured to perform a second set of one or more soil nutrient measurements; and
a second moisture sensor on the exterior of the side surface of the housing at the second location.

18. The device of claim 17, further comprising a soil penetrating tip disposed at a bottom surface of the housing.

19. The device of claim 17, further comprising a water reservoir operable to expel water adjacent the plurality of sensing surfaces when the moisture sensor detects a moisture level below a predetermined minimum.

20. The device of claim 17, further comprising:
automation circuitry configured to receive signals from the first and second plurality of sensing surfaces, the first and second reference electrodes and the first and second moisture sensors, wherein the automation circuitry includes:
a wireless transceiver configured to send and receive data from the soil nutrient measurement device;
a processor and memory for storing data received from the reference electrode and the one or more sensing surfaces; and
a GPS device for detecting a location of a measurement made by the one or more sensing surfaces.

\* \* \* \* \*